United States Patent

Bosetti et al.

[11] Patent Number: 5,698,731
[45] Date of Patent: Dec. 16, 1997

[54] PROCESS FOR THE PRODUCTION OF AROMATIC CARBAMATES

[75] Inventors: Aldo Bosetti, Vercelli; Pietro Cesti, Novara; Fausto Calderazzo, Pisa, all of Italy

[73] Assignee: Ministero dell 'Universita' e della Ricerca Scientifica e Tecnologica, Rome, Italy

[21] Appl. No.: 671,212

[22] Filed: Jun. 27, 1996

[30] Foreign Application Priority Data

Jul. 6, 1995 [IT] Italy .................. MI95A1445

[51] Int. Cl.$^6$ ............................... C07C 261/00
[52] U.S. Cl. ............ 560/24; 560/25; 560/26; 560/27; 560/28; 560/29; 560/30; 560/31; 560/32; 560/33
[58] Field of Search ............... 560/24, 25, 26, 560/27, 28, 29, 30, 31, 32, 33

[56] References Cited

U.S. PATENT DOCUMENTS

| 3,763,217 | 10/1973 | Brill . | |
| 4,268,683 | 5/1981 | Gurgiolo | 560/24 |
| 4,268,684 | 5/1981 | Gurgiolo . | |
| 4,395,565 | 7/1983 | Romano et al. . | |
| 4,550,188 | 10/1985 | Frulla | 560/24 |
| 4,567,287 | 1/1986 | Frulla | 560/24 |
| 5,091,556 | 2/1992 | Calderoni | 560/24 |

OTHER PUBLICATIONS

Chemical Abstracts, vol. 92, No. 25, AN 215096w, p. 591, 1980, T. Onoda, et al., "Carbamate Esters".
Ser. No. 08/671,179 Jun. 27, 1996 pending.
Ser. No. 08/671,212 Jun. 27, 1996 pending.

*Primary Examiner*—Michael L. Shippen
*Attorney, Agent, or Firm*—Oblon, Spivak, McClelland, Maier & Neustadt, P.C.

[57] ABSTRACT

A process is described for the preparation of aromatic carbamates in which an organic carbonate in a stoichiometric quantity or in a quantity higher than the stoichiometric value is reacted with an aromatic amine operating in the presence of a carbamation catalyst, wherein this catalyst is selected from N,N-substituted carbamate complexes of zinc or copper.

The process gives high yields and selectivity in the useful reaction product.

10 Claims, No Drawings

PROCESS FOR THE PRODUCTION OF AROMATIC CARBAMATES

The present invention relates to a process for the preparation of aromatic carbamates from an organic carbonate and an aromatic amine in the presence of a carbamation catalyst, wherein said catalyst is selected from N,N-substituted carbamate complexes of zinc or copper.

Carbamates in general, and N-phenyl alkyl carbamates in particular, are valuable intermediates in the production of aromatic isocyanates used in the preparation of polyurethanes.

Various processes are known for the preparation of carbamates by the reaction of a carbonate and an aromatic amine in the presence of a catalyst of the Lewis acid type. For example, U.S. Pat. No. 3,763,217 describes the preparation of carbamates by the reaction, under reflux conditions, of an alkyl carbamate with an aromatic amine, in the presence of a Lewis acid, preferably uranyl nitrate. The quantity of Lewis acid used can vary from 0.1 to 10% and, preferably, from 0.5 to 1.0% in moles of the amine. Under these conditions the conversion and selectivity yields of the carbamate are about 20%.

U.S. Pat. No. 4,268,683 describes the preparation of mono- and dicarbamates by the reaction of an alkyl carbonate and an aromatic mono- or diamine, using a compound of Sn (II) or Zn (II) as Lewis acid, such as for example halides or salts of monovalent organic acids with a pKa equal to or higher than 2.8.

For example, operating in the presence of 1% in moles of catalyst on the amine conversion and selectivity yields of the carbamate of about 77% are obtained.

Operating according to these known processes, when the Lewis acid is used with a low molar ratio with respect to the amine, there is inevitably the formation of substantial quantities of by-product urea, even when operating with high molar ratios between carbonate and aromatic amine. Consequently the production of carbamates with good yields requires operating with high contents of catalyst, which is disadvantageous both economically and from the point of view of the separation and purification treatment of the end-products.

A simple and convenient process has now been found which enables the preparation of carbamates from carbonates and aromatic amines, with practically complete yields and selectivities of the useful reaction product using N,N-substituted carbamate complexes of zinc or copper, as catalyst.

In accordance with this, the present invention relates to a process for the preparation of aromatic carbamates by the reaction of an organic carbonate with an aromatic amine operating in the presence of a catalyst, characterized in that said catalyst is selected from N,N-substituted carbamate complexes of zinc or copper definable with the general formula (I):

$$N_xO_y(OCONR')_z \quad (I)$$

wherein: N represents a metal selected from zinc or copper; x is an integer varying from 1 to 4; y is an integer varying from 0 to 1; z is an integer varying from 1 to 6 and R' represents a $C_1$–$C_{12}$ alkyl radical with a linear or branched chain, a $C_5$–$C_7$ cycloalkyl radical or aryl radical.

Examples of $C_1$–$C_{12}$ alkyl radicals for R' are methyl, ethyl, propyl, isopropyl, butyl, hexyl and dodecyl. $C_5$–$C_7$ cycloalkyl radicals for R' are cyclopentyl, cyclohexyl and cycloheptyl. Aryl radicals for R' are phenyl and naphthalene.

Catalysts having formula (I) which can be used for the present invention are:

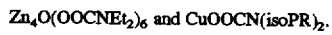

These catalysts can be prepared according to the method described in Inorg. Chem., 30: 3778–3781, 1991.

Organic carbonates which can be used in the process of the present invention comprise alkyl, aryl or alkyl aryl esters of carbonic acid. The ester group can be an alkyl group with up to 12 carbon atoms, preferably up to 6, or an aryl group with up to 10 carbon atoms.

Examples of organic carbonates particularly suitable for the process of the present invention are cyclic or acyclic carbonates such as for example ethylene carbonate, propylene carbonate, styrene carbonate, dimethyl carbonate, diethyl carbonate, dipropyl carbonate, dibutyl carbonate, diisopropyl carbonate, dihexyl carbonate, methyl butyl carbonate, diphenyl carbonate and methyl phenyl carbonate.

The organic carbonates can be prepared with the conventional methods.

Aromatic amines which can be used in the process of the present invention can be primary or secondary amines, preferably primary amines comprising monoamines, diamines, triamines, etc.

Examples of aromatic amines comprise those represented with the following formulae:

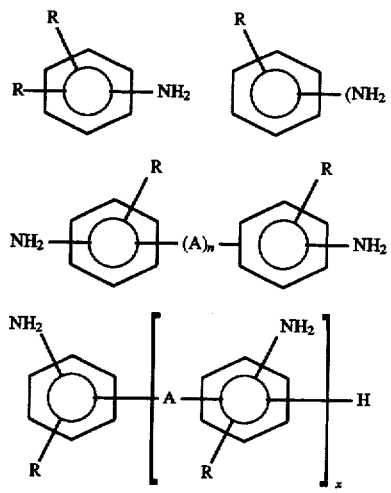

wherein R is hydrogen, a halogen, or a hyrocarbyl or hydrocarbyloxy group with up to 8, preferably up to 4, carbon atoms, A is a divalent hydrocarbon group with from 1 to 6, preferably from 1 to 4, carbon atoms, n has the value of 0 or 1 and x has a value of between 1 and 6, preferably between 2 and 4.

Aromatic amines which are particularly suitable for the process of the present invention are, for example, aniline, 3,4-dichloro aniline, ortho-, meta- and para-toluidine, 2,4-xylidene, 3,4-xylidine, 2,5-xylidine, 3-propyl aniline, 4-isopropyl aniline, methyl aniline, ethyl aniline, isopropyl aniline, butyl amine, heptyl amine, 4,4'-diamino-diphenyl methane, 2,4,4'-triamino diphenyl ether, 2,6-diamino naphthalene, 4,4'bismethylene diphenylamine, 4,4'-methylenedianiline.

Exmaples of carbamates which can be prepared with the process of the present invention are: N-methylphenylcarbamate, N-butylphenylcarbamate, N-pentylphenylcarbamate, N-hexylphenylcarbamate, 4,4'-methylenedimethyldiphenylcarbamate.

The carbonate and amine are interacted in the presence of the catalyst to produce the desired aromatic carbamate.

To obtain a complete conversion of the amine to carbamate, the carbonate must be present in at least an equivalent stoichiometric ratio. It is generally preferable to use the carbonate in excess with respect to the amine to minimize the side-reactions. It is advantageous to use a molar ratio between carbonate and amine of between 30/1 and 1/1, preferably between 10/1 and 5/1.

The quantity of catalyst used in the reaction can vary from 15 to 0.01%, preferably from 8 to 0.1%, per mole of amine.

The reaction temperatures can conveniently vary from 100° to 250° C. Temperatures below the first limit indicated can be used, but this is disadvantageous owing to the low reaction rate, whereas temperatures above the second limit indicated are disadvantageous as they favour the formation of reaction by-products. Temperatures of about 150°–170° C. are preferably used.

Operating under the above conditions a complete conversion of the amine is generally obtained in times of about 1–15 hours.

The carbamation reaction can be carried out in a stainless steel pressure-resistant reactor. The operating pressure is that given by the system itself.

At the end of the reaction the carbamate contained in the mixture is isolated and purified. The operations are conveniently carried out in two phases i.e. removal of the residual carbonate and purification of the carbamate. The removal of the carbonate is carried out by evaporation of the reaction mixture. In practice at the end of the reaction the pressure of the system is slowly lowered, bringing the temperature at the bottom to 100° C. and maintaining these conditions while the carbonate is distilled until it has been completely removed. The carbamate is then purified with the conventional techniques.

The process of the present invention basically has the advantage of transforming the amine into the relative carbamate with practically total yields, using reduced quantities of catalyst and bland operating conditions. There are obvious economical advantages of the process, including improved specifications as regards consumption of catalyst and amine.

The following experimental examples are illustrative but do not limit the scope of the present invention.

EXAMPLE 1

9.2 g (0.099 moles) of aniline, 43.8 g (0.486 moles) of dimethylcarbonate and 0.78 g (0.0008 moles, 1.0% per mole of aniline) of anhydrous zinc N,N-diethylcarbamate are charged into a cylindrical steel pressure-resistant reactor with a useful volume of 100 ml. After charging, the reactor is immersed in an oil-bath thermostat-regulated at 170° C. and magnetically stirred at about 300 rpm. The reaction is carried out at a pressure of 8 atms ($P_{max}$) for two hours. After cooling, the raw reaction product is analyzed via HPLC (RP-18 column, eluant water/acetonitrile 60/40, v/v, flow 1.5 ml/minute) obtaining:

| | |
|---|---|
| phenylmethylcarbamate | 99% |
| diphenylurea | 0.7% |
| N-methylaniline | 0.2% |

From these results it is possible to calculate the following conversion and selectivity values:

conversion ≧99% with respect to the aniline,
selectivity 99% per mole with respect to the phenyl methylcarbamate
yield 98%

After purifying the raw product with a silica gel column, eluant hexane/ethyl acetate (90/10, v/v) the following products are obtained:

| | |
|---|---|
| phenylmethylcarbamate | 14.5 g |
| diphenylurea | 0.10 g |

From these results an yield of 97% is calculated for the isolated product with respect to the initial aniline.

EXAMPLE 2

The same procedure is carried out as in example 1, carrying out the reaction in an oil bath thermostat-regulated at 140° C., at a pressure of 6 atms ($P_{max}$) for 3 hours. At the end of the reaction the raw product is analyzed obtaining:

| | |
|---|---|
| phenylmethylcarbamate | 77% |
| diphenylurea | 1.5% |
| N-methylaniline | 0.4% |
| aniline | 21% |

From these results it is possible to calculate the following conversion and selectivity values:

conversion 79% with respect to the aniline,
selectivity 97.5% per mole with respect to the phenylmethyl carbamate
yield 77%

After purification of the raw product the following products are obtained:

| | |
|---|---|
| non-reacted aniline | 1.9 g |
| phenylmethylcarbamate | 11.5 g |
| diphenylurea | 0.24 g |
| N-methylaniline | 0.032 g | yield 77% with respect to the initial aniline.

EXAMPLE 3

The same procedure is carried out as in example 1, using 1.54 g (0.00158 moles, 1.5% per mole of aniline) of anhydrous zinc N,N-diethylcarbamate. At the end of the reaction the raw product is analyzed by HPLC obtaining:

| | |
|---|---|
| phenylmethylcarbamate | 99% |
| diphenylurea | 0.7% |
| N-methylaniline | 0.1% |

From these results it is possible to calculate the following conversion and selectivity values:

conversion ≧99% with respect to the aniline,
selectivity equal to 99% per mole with respect to the phenylmethylcarbamate
yield 98%

After purification the following products are obtained:

| | |
|---|---|
| phenylmethylcarbamate | 14.4 g |
| diphenylurea | 0.14 g | yield 96% with respect to the initial aniline.

EXAMPLE 4

The same procedure is carried out as in example 3, carrying out the reaction at 130° C., at a pressure of 4 atms for 11 hours. At the end of the reaction the raw product is analyzed by HPLC obtaining the following results:

| | |
|---|---|
| aniline | 4.0% |
| phenylmethylcarbamate | 94.5% |
| diphenylurea | 0.7% |
| N-methylaniline | 0.4% |

From these results it is possible to calculate the following conversion and selectivity values:

conversion 96% with respect to the aniline, selectivity equal to 98% per mole with respect to the phenylmethylcarbamate yield 94%

After purification the following products are obtained:

| | |
|---|---|
| phenylmethylcarbamate | 14.0 g |
| diphenylurea | 0.13 g | yield 94% with respect to the initial aniline.

EXAMPLE 5

The same procedure is carried out as in example 1, using 32.1 g (0.36 moles) of dimethylcarbonate, 6 g (0.030 moles) of 4,4'-dimethylenedianiline (4,4'-MDA) and 0.48 g (0.0005 moles, 1.5% per mole of 4,4'-MDA) of anhydrous zinc N,N-diethylcarbamate. After charging, the reactor is immersed in an oil-bath thermostat-regulated at 160° C. and magnetically stirred at about 300 rpm. The reaction is carried out at a pressure of 7 atms ($P_{max}$) for three hours. After cooling, the raw reaction product is analyzed obtaining:

| | |
|---|---|
| 4,4'-methylenedimethyldiphenylcarbamate | 63% |
| urea | 16% |
| 4,4'-methylenemonodiphenylcarbamate | 0.2% |
| mixture of N-methyl derivatives | 20.8% |

From these results it is possible to calculate the following yield, conversion and selectivity values:

conversion 99% with respect to the initial 4,4'-MDA selectivity 63% per mole with respect to the 4,4'-methylenedimethyldiphenylcarbamate yield 62%

After purification the following products are obtained:

| | |
|---|---|
| 4,4'-methylenedimethyldiphenylcarbamate | 5.85 g |
| 4,4'-methylenemonomethylphenylcarbamate | 0.013 g |
| urea | 2.6 g |
| yield 62% with respect to the initial 4,4'-MDA. | |

EXAMPLE 6

(Comparative)

The same procedure is carried out as in example 2, using as catalyst 0.182 g of anhydrous zinc acetate (0.00094 moles, 1% per mole of aniline). At the end of the reaction the raw product is analyzed by HPLC obtaining:

| | |
|---|---|
| aniline | 13.0% |
| diphenylurea | 1.3% |
| N-methylaniline | 7.0% |
| phenylmethylcarbamate | 78.7% |
| conversion | 87% | selectivity 90% per mole with respect to the phenylmethyl carbamate.

yield 78% with respect to the initial aniline.

The data obtained in examples 1-6 are summarized in table 1 below.

TABLE 1

| Ex. | Catalyst (% on mole of amine) | T °C. | time hrs | P atm | Conversion % | Selectivity % |
|---|---|---|---|---|---|---|
| 1 | 1.0 | 170 | 2 | 8 | ≧99 | 99 |
| 2 | 1.0 | 140 | 3 | 6 | 79 | 97.5 |
| 3 | 1.5 | 170 | 2 | 8 | ≧99 | 99 |
| 4 | 1.5 | 130 | 11 | 4 | 96 | 98 |
| 5 | 1.5 | 160 | 3 | 7 | 99 | 63 |
| 6C | 1.0 | 140 | 3 | 8 | 87 | 90 |

EXAMPLE 7

9.2 g (0.099 moles) of aniline, 43.8 g (0.486 moles) of dimethylcarbonate and 1.36 g (0.00653 moles, 6.6% in moles) of anhydrous copper N,N-diisopropylcarbamate are charged into a cylindrical steel pressure-resistant reactor with a useful volume of 100 ml.

After charging, the reactor is immersed in an oil-bath thermostat-regulated at 170° C. and magnetically stirred at about 300 rpm. The reaction is carried out at a pressure of 8 atms ($P_{max}$) for 12 hours. At the end of the reaction, the raw product is analyzed via HPLC obtaining:

| | |
|---|---|
| aniline | 2% |
| phenylmethylcarbamate | 93% |
| diphenylurea | 1.3% |
| N-methylaniline | 3.5% |

From these results it is possible to calculate the following conversion and selectivity values:

conversion 98% with respect to the aniline, selectivity equal to 95% per mole with respect to the phenylmethylcarbamate yield 93% with respect to the initial aniline After purification the following products are obtained:

| | |
|---|---|
| phenylmethylcarbamate | 13.6 g |
| diphenylurea | 0.26 g |
| N-methyl aniline | 0.36 g |
| aniline | 0.18 g | yield 91% with respect to the initial aniline.

We claim:

1. A process for the preparation of aromatic carbamates from alkyl carbonates and aromatic amines in the presence of a carbamation catalyst characterized in that said catalyst is selected from N,N-disubstituted carbamate complexes of zinc or copper definable with the general formula (I)

$$N_xO_y(OCONR'_2)_z \qquad (I)$$

wherein: N represents a metal selected from zinc or copper; x is an integer with a value of between 1 and 4; y is an integer with a value of between 0 and 1; z is an integer with a value of between 1 and 6 and R' represents a $C_1$–$C_{12}$ alkyl radical with a linear or branched chain, a $C_5$–$C_7$ cycloalkyl radical or aryl radical.

2. The process according to claim 1, characterized in that R' is selected from methyl, ethyl, propyl, isopropyl, butyl, hexyl, dodecyl, cyclopentyl, cyclohexyl and cycloheptyl, phenyl and naphthalene.

3. The process according to claim 1, characterized in that the organic carbonate is selected from ethylene carbonate, propylene carbonate, styrene carbonate, dimethyl carbonate, diethyl carbonate, dipropyl carbonate, dibutyl carbonate, diisopropyl carbonate, dihexyl carbonate, methyl butyl carbonate, diphenyl carbonate and methyl phenyl carbonate.

4. The process according to claim 1, characterized in that the aromatic amine is selected from: aniline, 3,4-dichloro aniline, ortho-, meta- and para-toluidine, 2,4-xylidene, 3,4-xylidine, 2,5-xylidine, 3-propyl aniline, 4-isopropyl aniline, methyl aniline, ethylaniline, isopropyl aniline, butyl amine, heptyl amine, 4,4'-diamino-diphenyl methane, 2,4,4'-triamino diphenyl ether, 2,6-diamino naphthalene, 4,4'-bismethylene diphenylamine, 4,4'-methylenedianiline.

5. The process according to claim 1, characterized in that the molar ratio between the carbonate and the amine is between 30/1 and 1/1.

6. The process according to claim 5, characterized in that the molar ratio between the carbonate and amine is between 10/1 and 5/1.

7. The process according to claim 1, characterized in that a quantity of catalyst of between 15% and 0.01% per mole of amine, is used.

8. The process according to claim 7, characterized in that the quantity of catalyst is between 8 and 0.1% per mole of amine.

9. The process according to claim 1, characterized in that the operating temperature is between 100° and 250° C.

10. The process according to claim 9, characterized in that the temperature is between 150° and 170° C.

* * * * *